United States Patent [19]

Albarella et al.

[11] Patent Number: 5,079,140
[45] Date of Patent: Jan. 7, 1992

[54] AGENT FOR REDUCING ASCORBIC ACID INTERFERENCE IN LIQUID OR DRY PHASE ASSAY SYSTEMS AND METHOD RELATING THERETO

[75] Inventors: James P. Albarella, Elkhart; Lloyd A. Schick, Bristol; Meitak T. Yip, Elkhart, all of Ind.

[73] Assignee: Miles Inc., Elkhart, Ind.

[21] Appl. No.: 337,620

[22] Filed: Apr. 13, 1989

[51] Int. Cl.$^5$ .................. C12Q 1/00; G01N 1/00; C02F 1/72; C02F 5/10
[52] U.S. Cl. .................................. 435/4; 435/14; 435/25; 436/175; 436/129; 436/80; 210/759; 252/181
[58] Field of Search ............... 435/4, 7, 11, 14, 10, 435/28, 25, ; 436/175, 170, 169, 129, 80; 210/753, 759; 252/180, 181

[56] References Cited

U.S. PATENT DOCUMENTS

| | | |
|---|---|---|
| 4,743,559 | 5/1988 | Koever et al. ............ 436/175 |
| 4,910,134 | 3/1990 | Yamanishi et al. ......... 435/10 |
| 4,954,451 | 9/1990 | Albarella et al. .......... 436/175 |
| 4,957,872 | 9/1990 | Koever et al. ............ 436/175 |

Primary Examiner—Robert A. Wax
Assistant Examiner—David R. Preston
Attorney, Agent, or Firm—Roger N. Coe

[57] ABSTRACT

The present invention is directed to the elimination of ascorbic acid interference in assay systems, particularly assay systems based upon oxidase-peroxidase coupled reactions. When ascorbic acid is present in a sample, it can act as a reductant thereby interfering with an assay's reagent system. The present invention eliminates this inteference by quickly oxidizing any ascorbate thereby preventing ascorbate from acting as an unwanted reductant. The ascorbate is oxidized using a dual oxidant system comprising a water soluble polymer bound to $Cu^{+2}$ and an organic or inorganic oxidant such as chromate, peroxide, or a N-halo derivative. This invention is surprisingly selective and generally will not itself interfere with the assay's reagent system. Furthermore, the present invention is so fast and efficient that it can be incorporated into a convenient format, such as a conventional "dip-and-read" reagent test strip system.

4 Claims, No Drawings

AGENT FOR REDUCING ASCORBIC ACID INTERFERENCE IN LIQUID OR DRY PHASE ASSAY SYSTEMS AND METHOD RELATING THERETO

BACKGROUND OF THE INVENTION

1. Field of The Invention

This invention relates generally to a scavenger system which can eliminate ascorbic acid interference in a large number of liquid and dry phase assay systems, particularly assay systems based upon an oxidase-peroxidase coupled reaction such as conventional assays used to determine occult blood, cholesterol, triglycerides, uric acid and the like in body fluids. More specifically, this invention is directed to an agent which quickly and selectively oxidizes ascorbate (the ion form of ascorbic acid) in an analytical sample, such as urine, before the ascorbate is able to interfere with an assay's reagent system.

2. Discussion of the Prior Art

The most common form of ascorbic acid is typically referred to as Vitamin C. This vitamin is a vital nutrient and is found in many naturally occurring foods, such as fruits and vegetables. Vitamin C can also be synthesized and is therefore available as a food additive or in tablet form.

The health benefits of Vitamin C have been known for some time. Over a century ago, sailors discovered that they would become severely ill on long voyages unless they ate certain foods rich in this vitamin. Recent medical studies have suggested that large doses of Vitamin C can be therapeutic in treating the common cold. As a result, Vitamin C is a relatively popular nutrient and is therefore a popular food additive and a popular component of vitamin pills and the like.

However, a person's body will generally absorb Vitamin C only to the extent necessary to meet the body's short term needs. The vitamin is generally not stored within the body, and excess Vitamin C is typically disposed of by means of the body's urinary system. As a result, Vitamin C is commonly found in urine samples used in medical analysis and the like.

Urine analysis is an important part of modern health care, and substantial knowledge concerning a patient's physiological condition can be obtained by monitoring urine components such as glucose, occult blood, cholesterol, triglycerides, or uric acid. However, many commonly known urine assay systems are adversely affected to some degree by ascorbic acid.

Ascorbate is a reductant which can interfere with an assay's reagent system. Many assays have redox indicator systems which will change color as the indicator changes from a reduced to an oxidized state due to the presence of an oxidizer. In a typical assay, the reagent system is designed to cause redox indicator oxidation in proportion to the amount of analyte in a sample. As a reductant, ascorbate can interfere with such systems.

However, ascorbate can be oxidized and if ascorbate is oxidized before it interferes with an assay system the ascorbate will not be able to act as a reductant and therefore will not cause interferance.

A number of systems are known which are directed to the oxidation of ascorbate. Pecht, I., et al., "The Copper-Poly-L-Histidine Complex: I. The Environmental Effect of the Polyelectrolyte on the Oxidase Activity of Copper Ions", *J. Am. Chem. Soc.*, 89:1587, (1968) shows that ascorbate can be oxidized by means of oxygen and a copper catalyst. Also, polyhistidine (PLH) is shown to enhance the catalytic efficiency of copper II towards negatively-charged and neutral substrates such as ascorbate.

Vengerova, N.A., Kirsh, Y.E. and Kabanov, V.A., "The ascorbate-oxidase activity of the $Cu^{+2}$-poly-4-vinylpyridine complex alkylated with bromoacetic acid." Vysokomol. soyed., A 13, No. 11, pp. 2509–2517 (1971) (translated by K.A. Allen) shows a method of synthesizing carboxymethyl derivatives of poly-4-vinyl-pyridine and shows that a Cu II polymer complex will increase ascorbate oxidizing activity relative to copper ions alone.

It is also known that a histamine-latex can be synthesized and added to $CuSO_4$ to make the complex-latex-histamine-Cu(II). The complex behaves as a Michaelis-Menten catalyst and has been found to be stable and reusable as a catalyst for the oxidation of ascorbic acid. See generally, Sun, Z., Jan, C., and Ketano, H., "Studies on Functional Latices: Catalytic Effects of Histamine-containing Polymer-latex-copper (II) Complex on the Oxidation of Ascorbic Acid." *Macromolecules*, 19:984–987 (1986).

It is also known that ascorbic acid can be oxidized with molecular oxygen catalyzed by a complex of copper II and poly-4-vinyl-pyridine. The mechanism involves the interaction of copper II with the ascorbate anion to yield copper I ions. Another stage of the catalytic effect is the oxidation of copper I by molecular oxygen. See generally, Skurlator, Y.I. et al., "The Mechanism of Ascorbic Acid Oxidation by Cu(II)-poly-4-vinyl-Pyridine Complexes." *European Polymer Journal*, 15:811–815 (1979).

Also, European Patent Application 0037056 describes the use of iodate in diagnostic methods to avoid interference by reducing agents, including ascorbic acid. U.S. Pat. No. 4,288,541, by Magers, "Ascorbate Resistant Composition Test Device and Method for Detecting a Component in Liquid Test Sample", discloses the use of mercuric ion complex as a scavenger system for the removal of ascorbic acid in a test device for urinary glucose.

Many of the above references relate to the oxidation of ascorbate by reducing $Cu^{+2}$ to $Cu^{+1}$. However, $Cu^{+1}$ is also a reductant and therefore will interfere with an assay in a manner similar to nonoxidized ascorbate. The Vengerova reference re-oxidizes $Cu^{+1}$ to $Cu^{+2}$ using oxygen. However, oxygen can be a very inconvenient reagent, since it is a gas at room temperature. Furthermore, all of the ascorbate oxidizing substances discussed in the above-mentioned articles are insoluble in water and organic solvents. As such, it would be very difficult to apply the substances as a uniform coating on film and therefore they would not be suitable for a dry reagent system, such as a conventional dip-and-read reagent test strip system. Furthermore, the prior art substances do not have sufficient reactivity to remove (scavenge) ascorbate at a rate sufficient to prevent unwanted interference with a conventional redox indicator system.

Consequently, it is an object of the present invention to provide an agent which can be used in an assay system to oxidize (scavenge) ascorbate at a rate sufficient to prevent unwanted ascorbate interference.

A further object of this invention is to provide an ascorbate scavenger system which can be incorporated into a conventional "dip-and-read" reagent test strip.

Other objects and features of the present invention will become obvious to those of ordinary skill in the art upon reading the following specification.

SUMMARY OF THE INVENTION

The present invention is directed to the elimination of ascorbic acid interference in assay systems, particularly assay systems based upon oxidase-peroxidase coupled reactions. When ascorbic acid is present in a sample, it can act as a reductant and interfere with an assay's reagent system. The present invention eliminates this interference by quickly oxidizing ascorbate, thereby preventing ascorbate from acting as an unwanted reductant. The ascorbate is oxidized using a dual oxidant system comprising a water soluble polymer which is bound to $Cu^{+2}$ and an organic or inorganic oxidant such as chromate, peroxide, or a N-halo derivative. This invention is surprisingly selective and generally will not itself interfere with the assay's reagent system. Furthermore, the present invention is so fast and efficient that it can be incorporated into a convenient format, such as a conventional "dip-and-read" reagent test strip system.

DETAILED DESCRIPTION OF THE PREFERRED EMBODIMENTS

The present invention is directed to a dual oxidant system which eliminates ascorbate interference for many assay systems without itself causing any significant assay interference. Oxidant I is a water soluble polymer which is bound to $Cu^{+2}$ (the more water soluble the polymer, the more preferred it is for use in the present invention). The polymer-$Cu^{+2}$ complex preferably becomes a homogeneous gel-like complex in aqueous solution when bound to $Cu^{+2}$.

The most preferred copper ligand complex (oxidant I) comprises a histamine or pyridine ligand complexed with $Cu^{+2}$, said copper-ligand complex having a water soluble polymer backbone of the formula:

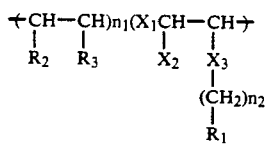

where:
$n_1 = 0$ to 3
$n_2 = 1$ to 3
$R_1 =$ imidazolyl or pyridyl
$R_2 =$ H or carboxyl or alkoxy
$R_3 =$ H or carboxyl or alkoxy
$X_1 = -O-$ or $-NR_4-$, where $R_4$ is H or lower alkyl of 1 to 6 carbon atoms, or H
$X_2 =$ H or carboxyl
$X_3 = -CONH-$ or $-(CH_2)n_3-NH-$, wherein $n_3$ is 0 to 3 or 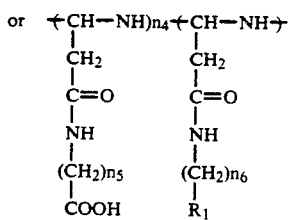

where:
$n_4$, $n_5$ and $n_6 = 1$ to 3
$R_1 =$ imidazolyl or pyridyl

The second oxidant (Oxidant II) can be an inorganic oxidant, organic peroxide or organic N-halo derivative. Examples of inorganic oxidants include chromate, bromate, iodate, mercuric, thallium (III), ceric(IV), and manganese (III) compounds wherein chromate, bromate and iodate are most preferred. Examples of organic peroxides include diisopropylbenzene dihydroperoxide (DBDH), diisopropylbenzene monohydroperoxide, phenylcyclohexane hydroperoxide, p-($\alpha$-hydroperoxyisopropyl) benzoic acid, p-bromoisopropyl) benzene hydroperoxide and p-($\alpha$-hydroxy-$\alpha'$-hydroperoxyisopropyl)benzene, wherein DBDH is most preferred. An example of an organic N-halo compound is 1-halobenzotriazole.

The $Cu^{+2}$ polymer complex of Oxidant I is selectively reduced by ascorbate into $Cu^{+1}$, and Oxidant II continuously and selectively reoxidizes the copper (I) to the $Cu^{+2}$ form. Although either oxidant alone does not provide sufficient reactivity to effectively oxidize ascorbate at the highest concentration level generally expected in urine, i.e. 200 mg/dL (or 11 mM), the combination of oxidants effectively eliminates ascorbate interference in many assay systems even with ascorbate concentrations of greater than 200 mg/dL (milligrams per deciliter).

Since Oxidant II is used to recycle the reduced Cu (I):polymer back to its original Cu (II):polymer, the Oxidant II should be present in an amount in excess over the amount of ascorbic acid present.

Theoretically, the Cu (II) :polymer can be present in catalytic quantities (less than equimolar with ascorbic acid) in order to oxidize all of the ascorbic acid as long as the Oxidant II is in excess. In practice, the rate of ascorbic acid oxidation is proportional to the concentration of both Oxidant I and Oxidant II. The practical upper limit of the concentration of Oxidant I and Oxidant II is determined by solubility constraints or competing acid reactions.

A preferred ratio of Oxidant II to Oxidant I is in the range of 1:1 to 10:1 and a particularly preferred ratio is about 2:1.

Generally, for the application of these reagents to the solid phase Oxidant I is applied in an aqueous solution and Oxidant II is applied in a nonaqueous, separate step.

The ascorbate scavenging system of this invention is specific. The system can scavenge ascorbic acid without adversely affecting an assay's reagent system, particularly an assay's redox indicator system or otherwise inhibiting any enzymes found in an assay or sample.

The system is also rapid. The oxidation rate is sufficiently rapid in either solution or solid phase such that the system is effective in removing ascorbic acid interference even though an assay's color development reaction in response to an analyte of interest, such as glucose, is also relatively fast and is also based upon an oxidation reaction.

The water soluble polymer consists of two parts: the first part is the water soluble polymer backbone such as (1) the hydrolyzed form of Gantrez ™ (poly[methylvinyl ether/maleic acid]) (Gantrez is the trademark of a product of GAF Corporation, New York, New York)

-continued

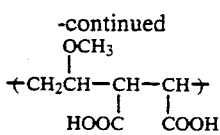

(2) polyacrylic acid

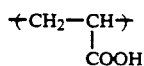

(3) polyaspartic acid

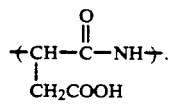

The second part is the ligands required to coordinate to Cu such as imidazole, pyridine or 2,2'-bipyridine.

(1) Poly[2-carboxy-1-(2-imidazol-4'-yl-ethyl)carbamoyl-3-methoxy-butylene/1,2-dicarboxy-3-methoxybutylene] Histamine-Gantrez

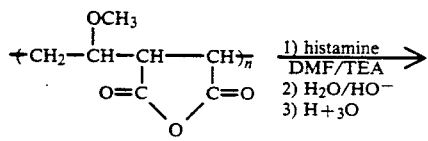

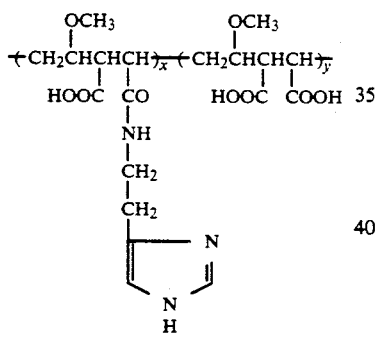

Under argon, Gantrez AN-119 TM (12.48 g, 80 mmole of anhydride, MW=19,000, GAF Corporation, New York, N.Y.) was dissolved in 200 mL of anhydrous DMF in a 65° C. oil bath. Then a solution of histamine (8.88 g, 80 mmole, Aldrich Chenmical Co., Inc., Milwaukee, Wis., USA) and triethylamine (11.12 mL, 80 mmole, Aldrich Chemical Company, Inc.) in 200 mL of anhydrous DMF was added dropwise in a period of 25 minutes. The reaction mixture was then stirred in a 65° C. oil bath for 20 hours, 400 mL of water was added and the resulting mixture was stirred for about 5 hours. The reaction mixture was then cooled in an ice bath to room temperature and the pH (9.6) was adjusted to 6.4 with 3N HCl. At this point, a brown gummy material separated. The supernatant was decanted and the gummy material was washed with water very quickly twice, then mixed with acetone and was allowed to stand at room temperature for 20 hours. The gummy material solidified and was ground into fine powder and washed with THF and acetone thoroughly and then dried in vacuo to give 13.5 g of a beige solid. (Yield 63%)

IR (KBr) cm$^{-1}$:3450; 2900; 1702; 1650; 1572; 1453; 1384; 1087; 695.

Analysis: calculated for x=90%, y=10% or histamine/COOH=45/55. C, 53.54; H, 6.37; N, 14.66
Found: C, 53.25; H, 6.48; N, 14.64.

Cu-Histamine-Gantrez Complex

To a solution of histamine-Gantrez (4 g, about 15 mmole) in 100 mL of water was added 15 mL of 0.5M CuSO$_4$ solution (7.5 mmole). A blue precipitate separated out immediately. After mixing for 10 minutes, the solid was filtered and washed with 100 ml of water until the filtrate was colorless (about three times). The solid was then resuspended in 100 mL of water and lyophilized to give 3 g of a blue solid which can be suspended very easily in an aqueous solution.

(2) Poly[N$_\beta$-(2-imidazol-4'-yl-ethyl)-asparagine/N$_\beta$-(3-carboxypropyl)-asparagine]

Histamine-polyaspartic acid

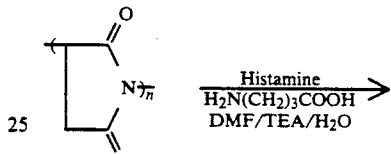

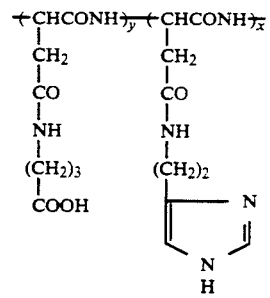

Under argon, histamine (3.42 g, 30.9 mmol, Aldrich Chemical Company, Inc.), 4-aminobutyric acid (3.18 g, 30.9 mmole, Aldrich Chemical Company, Inc.) and triethylamine (4.3 mL, 30.9 mmole) were dissolved in 40 mL of water and 30 mL of DMF. Then, a warm solution of polysuccinimide (3 g, 30.9 mmole, average MW=30,000) in 30 mL of anhydrous DMF was added and the resulting reaction mixture was stirred at room temperature for 20 hours. The reaction mixture was then dialyzed against 3.8 pl liter of water for three days during which time, fresh water was replaced three times per day. The polymer solution was then concentrated to give a honey colored gummy residue which was triturated with THF$^4$ several times to give 2.7 g of a beige solid.

About 1 g of the crude histamine-polyaspartic acid was dissolved in 3 mL of water and the pH of the solution (7.4) was adjusted to 5.4 with 3N HCl. The solution was loaded onto a Bio-gel P6DG (Bio-Rad Laboratories, Richmond, California, USA) column (2.5×60 cm) and eluted with water. Fractions containing only the polymer, as indicated by TLC (CHCl$_3$/MeOH/NH$_3$, 50/40/4, v/v/v, followed by I$_2$ spray), were combined and lyophilized to give 0.7 g of a beige solid.

IR (KBr) cm$^{-1}$:3400 (br); 1630; 1520; 1380.

Analysis: Calculated for M.1/2H$_2$O where x=51% or histamine/COOH=51/49, C, 47.58; H, 6.15; N, 19.83
Found: C, 47.63; H, 5.90; N, 20.13.

Cu-Histamine Polyaspartic Acid Complex

The Cu-histamine-polyaspartic acid complex was prepared by mixing 20 mM of CuSO₄ and 40 mM histamine-polyaspartic acid solution.

(3) Poly[N-(2-imidazol-4'-yl- ethyl)acrylamide/-acrylic acid]

Histamine-polyacrylic acid

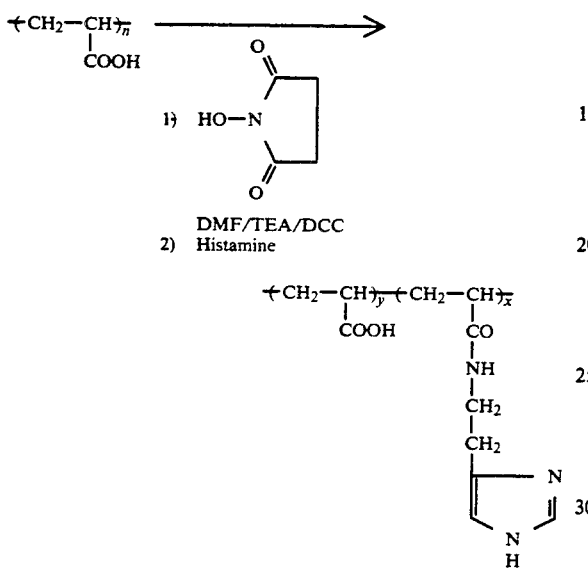

Under argon, polyacrylic acid (2.52 g, 35 mmole, average MW=2,000 Aldrich Chemical Company, Inc.) was dissolved in 75 mL of warm anhydrous DMF. The solution was cooled to room temperature and then a solution of N-hydroxysuccinimide (2.6 g, 45 mmole, Aldrich Chemical Company, Inc.) in 12 mL of anhydrous DMF, a solution of 1,3-dicyclohexylcarbodiimide (4.65 g, 45 mmole, Aldrich Chemical Company, Inc.) in 12 mL of anhydrous DMF and triethylamine (4.85 mL, 35 mmole) were added and the resulting reaction mixture was stirred for 22 hours at room temperature. A large amount of urea separated out and was filtered off to give a very light yellow solution of NOS activated polyacrylic acid.

Under argon, to a solution of histamine (2.5 g, 22.5 mmole, Aldrich Chemical Company, Inc.) in 50 mL of anhydrous DMF was added dropwise the solution of NOS activated polyacrylic acid in a period of 10 minutes and the resulting reaction mixture was stirred at room temperature for 22 hours. Then 60 mL of water was added and the mixture was stirred for 5 hours, the pH was adjusted to neutral with 3N HCl and the solution was concentrated to give a viscous liquid. On addition of an equal volume of acetone, a gummy material separated out, the supernatant was decanted and the residue was rinsed with water quickly twice. The gummy material was then triturated with acetone twice to give a hard solid which was ground to a fine powder and washed with acetone and THF to give a white solid of crude histamine-polyacrylic acid.

The crude histamine-polyacrylic acid was purified by dissolving in 5 mL of water and then loading it onto a Bio-gel P6DG (Bio-Rad Laboratories) column (2.5×60 cm) and eluting with water. Fractions containing only the polymer as indicated by TLC (CHCl₃/MeOH/NH₃, 50/40/4, v/v/v; followed by I₂ spray) were combined and lyophilized to give 0.5 g of a white solid.

IR (KBr) cm⁻¹: 3426; 1637; 1562; 1546; 1403.

Analysis: Calculated for M.1/10 H₂O where x=35% or histamine/COOH=35/65. C, 53.59; H, 6.30; N, 13.81.

Found: C, 53.54; H, 6.41; N, 14.21.

Cu-histamine-polyacrylic acid complex

The Cu-histamine-polyacrylic acid complex was prepared by mixing 20 mM of CuSO₄ and 40 mM of histamine-polyacrylic acid solution.

(4) Poly[2-carboxy-3-methoxy-1-(pyrid-4-yl-methyl)-carbamoylbutylene/1,2-dicarboxy-3-methoxy-butylene]

Pyridine-Gantrez

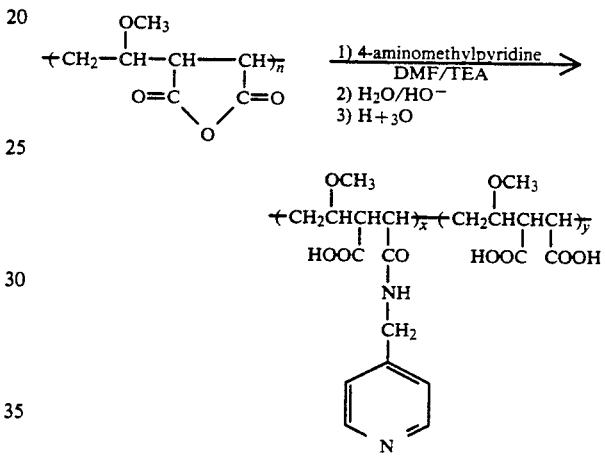

Under argon, Gantrez AN-119 ™ (6.24 g, 40 mmole, MW=19,000, GAF Corporation, New York) was dissolved in 100 mL of anhydrous DMF at 40° C. Then triethylamine (5.6 mL, 40 mmole) was added. A solution of 4-aminomethylpyridine (4.32 g, 49 mmole, Aldrich Chemical Company, Inc.) in 100 mL of anhydrous DMF was then added dropwise in a period of 12 minutes and the resulting reaction mixture was stirred at 40° C. for 20 hours. Water (110 mL) was added and the mixture was stirred for 3 hours. The pH of the mixture (8.8) was then adjusted to 4.9 with 3N HCl. A large amount of gummy material separated out. The supernatant was decanted and the mass was rinsed with water quickly twice. The gummy material was then triturated with acetone and THF and dried in vacuo to give 4.26 g of a white solid.

Analysis: Calculated for x=76% or pyridine/COOH=38/62. C, 57.22; H, 6.05; N, 8.78.

Found: C, 57.56; H, 6.14, N, 8.55.

Cu-Pyridine-Gantrez

To a solution of pyridine-Gantrez (1 g, 4 mmole) in 25 ml of water was added 4 mL of 0.5M CuSO₄ solution. After mixing for several minutes, the mixture was filtered, washed with water several times, resuspended in 30 ml of water and lyophilized to give 1.4 g of a blue solid which can be suspended easily in aqueous solution.

EXAMPLES

Example 1

A reagent matrix was created by preparing a sheet of microporous polyurethane which was obtained by wet casting the polymer mixture onto a nonporous plastic support followed by a water bath coagulation and then drying. The microporous polyurethane consisted of the following solution:

- 3.2%— KBH 672 polyurethane
- 0.9%— Dralon U
- 5.3%— Mowilith
- 4.3%— KPK Pt 144 Cationic Polyurethane Dispersion
- 18.2% Talkum AT1
- 0.4% Dodecyl Benzene Sulfonate in Dimethylformamide.

The suspension was cast onto Hostaphan (polyethyleneterephthlate) using a knife over roller technique. The material was passed through a water bath and dried at 50° C. The resulting polyurethane sheet on polyethylene terephthlate (PET) is, accordingly, the nonporous plastic support.

A solution consisting of 100 mM (millimolar) 3,3',5,5' tetramethylbenzidine (TMB) and 50 mM Aerosol OT in 1-methoxy-2-propanol was applied to the matrix as a coating using a Mayer rod. After drying for 10 minutes at 50° C., the matrix was treated with a second solution consisting of 10 mg/mL (milligrams per milliliter) peroxidase, 5 mg/mL glucose oxidase and 1% Triton™ X-100 in 0.2 M phosphate (pH 7.0). The matrix was dried at 50° C. for 10 minutes. Finally, a solution consisting of 20 mM CuSO$_4$, 40 mM histamine-GANTREZ, and 20 mM potassium chromate in 0.2 M phosphate (pH 7.0) was applied to the matrix and the matrix was dried at 50° C. for 10 minutes. The reagent-treated matrix was backed with double-sided adhesive, cut into 0.5 centimeter wide ribbons, applied to the edge of white polystyrene backing, and slit to give individual reagent strips.

To test the effectiveness of the scavenger layer, a comparison was made between systems having varying amounts of the scavenger. First, reagent strips were dipped in urine standards containing 0, 20, 40, 60, 80, or 100 mg/dL glucose and at 60 seconds the pad reflectance was determined using a rapid scanner between 400–700 nm (nanometers). The reflectance measurements at 660 nm (the wavelength of maximum reflectance change) were used to prepare a standard curve of K/S at 660 nm versus glucose concentration in mg/dL. Next, the strips were dipped in urine standards containing 100 mg/dL glucose and either 50, 100, or 200 mg/dL ascorbic acid. Pad reflectance measurement at a 60 second read time were used to determine the observed glucose assignment for those urines containing ascorbic acid by reading the glucose level from the glucose standard curve.

The K/S ratio is derived from the Kubelka-Munk model which is designed to explain the light-scattering properties of colorant layers. Generally the K/S ratio of a component colorant is a function of concentration. According to the Kubelka-Munk theory:

$$K/S = \frac{(1 - R_\infty)^2}{2 R_\infty}$$

wherein:

$R_\infty$ is the reflectance of a layer so thick that further increase in thickness fails to change the reflectance;

K is the absorption coefficient, and is a measure of the fraction of the light flux by absorption in the elementary layer; and S is the scattering coefficient and is the fraction of light flux lost by having its direction reversed.

TABLE I

Ascorbate Scavenger Systems

| | pH | Actual Glucose (mg/dL) | Ascorbic Acid (mg/dL) | Observed Glucose (mg/dL) |
|---|---|---|---|---|
| Control (no scavenger) | 7.0 | 100 | 0 | 100 |
| | | 100 | 50 | 18 |
| | | 100 | 100 | 0 |
| | | 100 | 200 | 0 |
| 10 mM Cu(II) histamine-Gantrez plus 10 mM K$_2$CrO$_4$ | 7.0 | 100 | 0 | 100 |
| | | 100 | 50 | 79 |
| | | 100 | 100 | 77 |
| | | 100 | 200 | 65 |
| 20 mM Cu(II) histamine-polyacrylic acid plus 20 mM K$_2$CrO$_4$ | 7.0 | 100 | 0 | 100 |
| | | 100 | 50 | 92 |
| | | 100 | 100 | 76 |
| | | 100 | 200 | 49 |
| 20 mM Cu(II) histamine-polyaspartic acid plus 20 mM K$_2$CrO$_4$ | 7.0 | 100 | 0 | 100 |
| | | 100 | 50 | 80 |
| | | 100 | 100 | 72 |
| | | 100 | 200 | 61 |

The results in Table I show that the accuracy of the test results are dramatically improved when the scavenger system is present compared with those when no scavenger system is used. In addition, Table I shows that several histamine-derivatized polymers can be used effectively, including histamine-polyacrylic acid and histamine-polyaspartic acid.

Example 2

Example of Ascorbate-Resistant Urine Glucose Strip Using DBDH Plus Cu(II)-Histamine Gantrez An experiment was carried out using diisopropyl benzene dihydroperoxide (DBDH) as the co-oxidant in a system using Copper(II)-Histamine-Gantrez as the catalyst. Reagent strips were prepared as described below and tested for color development response to urine glucose and resistance to interference by ascorbic acid.

The starting matrix consisted of a sheet of microporous polyurethane supported on a nonporous polycarbonate backing. The matrix was treated with reagents using a Mayer rod coating technique. The first application coating solution consisted of the following:

| 1st Application Formulation | |
|---|---|
| Peroxidase | 1 g (gram) |
| Glucose Oxidase | 0.5 g |
| 0.5 M Phosphate (pH 7.0) | 40 mL |
| Triton X-100 | 1 g |
| FD & C Yellow #5 | 0.01 g |
| Cu(II).Histamine-Gantrez | 0.98 g (20 mM final) |
| H$_2$O | 58 mL |
| | 100 mL |

The matrix was dried at 50° C. for 10 minutes. Then the matrix was treated using the same technique with a second application solution consisting of the following:

| 2nd Application Solution | |
|---|---|
| 3,3',5,5' tetramethyl-benzidine | 2.4 g |
| Aerosol OT | 2.2 g |
| DBDH | 0.452 g (20 mM final) |
| 1-methoxy-2-propanol | 90 g |
| | 100 g |

The matrix was dried at 50° C. for 10 minutes. The material was backed with double-sided adhesive with the microporous polyurethane facing out, cut into 0.5 centimeter wide ribbons applied to one edge of white polystyrene backing, and slit to give individual reagent strips.

The reagent strips were evaluated as described in Example 1. The results in Table II below show that the accuracy of the test results are improved when the strips containing DBDH plus Cu(II)-Histamine-Gantrez are compared with those without the scavenger system present.

TABLE II

| Formulation | Urine Glucose Level (mg/dL) | Ascorbic Acid Level (mg/dL) | Observed Glucose Level (mg/dL) |
|---|---|---|---|
| Control (no scavenger) | 100 | 0 | 100 |
| " | " | 50 | 18 |
| " | " | 100 | 0 |
| " | " | 200 | 0 |
| Test (20 mM Cu(II)-Histamine-Gantrez) 20 mM DBDH | 100 | 0 | 100 |
| " | " | 50 | 42 |
| " | " | 100 | 27 |
| " | " | 200 | 9 |

Similar experiments were carried out using other hydroperoxides, including cyclohexylbenzene hydroperoxide (CBH), and isopropylbenzoic acid hydroperoxide (IBH). These were effective in the solid phase as well.

EXAMPLE 3

The Use of Cu(II)-Pyridine-Gantrez Plus $K_2CrO_4$ as a Scavenger Systen for Ascorbic Acid copper II and 200 mM in histamine or pyridine. Other stock solutions used in this experiment were 0.5 M sodium phosphate buffer (pH 7.0), 0.1 M potassium chromate, 2000 mg/dL glucose standard and 10% ascorbic acid in distilled water.

The test for the removal of ascorbic acid interference by the scavenging system was carried out in 12×75 mm glass tubes. Components of the reaction mixture were added to the tubes in the amounts and in the order listed in Table III. Ten seconds after the addition of ascorbic acid, the presence or absence of ascorbic acid was determined by dipping a test strip of C-STIX ® (Miles Inc., Elkhart, Ind., USA) in the text mixture. At the same time, the ability to detect the presence of 100 mg/dL glucose was determined using glucose test strips not containing any reagents for scavenging ascorbic acid. Thus, if ascorbic acid was removed during the 10 second incubation period the strips would react immediately and develop a blue color.

If ascorbic acid was present, the test strip would develop no color at all or only after a lag time.

The results in Table IV show that Cu(II)-histamine-Gantrez plus potassium chromate or Cu(II)-pyridine-Gantrez plus potassium chromate are equally effective in removing ascorbic acid prior to testing for glucose. On the other hand, if either the Cu(II)-ligand-Gantrez catalyst or co-oxidant is missing, the C-STIX ® is positive and no color (or color only after a long lag) develops on glucose test strips.

TABLE III

| Copper Polymer System: | |
|---|---|
| Buffer: phosphate, 0.4 M, pH 7 | |
| Glucose: 100 mg/dL | |
| Ascorbic Acid: 100 mg/dL | |
| Oxidant 2: $K_2CrO_4$, 2.5 mM | |
| Concentration of Oxidant 1: 12.5 mM | |
| Oxidant 1 | Reactivity |
| Cu(II)-Histamine-Gantrez | ++++ |
| Cu(II)-Pyridine-Gantrez | ++++ |
| Cu(II)-Histamine-polyaspartic acid | ++++ |
| Cu(II)-Histamine-polyacrylic acid | ++++ |
| Cu(II)-Carboxymethylated Poly-4-vinylpyridine* | +++ [heterogeneous] |
| No oxidant | ++ |

*prepared according to the procedure described by Vengerova, Krish and Kabanov, supra.

TABLE IV

| | | | Cu(II)-Ligand-Polymer Catalyst | | | | | Results | |
|---|---|---|---|---|---|---|---|---|---|
| Tube No. | $H_2O$ | 0.5 M Phosphate (pH 7.0) | 100 mM Cu(II)-Histamine Gantrez | 100 mM Cu(II)-Pyridine Gantrez | 0.1 M $K_2CrO_4$ | 2000 mg/dl Glucose | 10% Ascorbic Acid | Glucose Strip | C-STIX |
| 1 | 0.54 mL | 0.2 mL | 0.1 mL | — | 0.1 mL | 50 μL | 10 μL | blue | negative |
| 2 | 0.54 | " | 0.1 mL | 0.1 mL | 0.1 | " | " | blue | negative |
| 3 | 0.64 | " | — | — | 0.1 | " | " | long lag; slight color | positive |
| 4 | 0.64 | " | 0.1 | — | — | " | " | no color | positive |
| 5 | 0.64 | " | — | 0.1 | — | " | " | no color | positive |
| 6 | 0.74 | " | — | — | — | " | " | no color | positive |
| 7 | 0.75 | " | — | — | — | " | " | blue | negative |

The effectiveness of Cu(II)-pyridine-Gantrez as a catalyst for the oxidation of ascorbic acid was determined in liquid studies and compared with that observed for Cu(II)-histamine-Gantrez.

A stock preparation of either Cu(II)-histamine-Gantrez or Cu(II)-pyridine-Gantrez was made by suspending 59.6 mg of the lyophilized powder in 1 mL of distilled water. This gave a suspension that is 100 mM in Example 4

The Use of Various Hydroperoxides as Co-oxidants and Cu(II)-Histamine-Gantrez as Catalyst for the Removal of Ascorbic Acid Interference Prior to Testing for Urine Glucose A similar experimental approach as in Example 3 was used to demonstrate the effectiveness of several different hydroperoxides as co-oxidants along with Cu(II)-histamine-Gantrez for the removal of ascorbic acid interference prior to testing for urine glucose. Stock solutions in ethanol were prepared containing 100 mM level of cyclohexylbenzene hydroperoxide (CBH), diisopropylbenzene dihydroperoxide (DBDH), isopropylbenzoic acid hydroperoxide (IBH), or para-bromoisopropylbenzene hydroperoxide (BIPBH). Components of the reaction mixture were added to a 12×75 mm tube in the amounts and in the order listed in the accompanying Table V. Ten seconds after the addition of ascorbic acid, the presence or absence of ascorbic acid was determined using C-STIX ®, and glucose was detected using glucose test strips as before.

The results in Table V show that Cu(II)-histamine-Gantrez plus 10 mM of either CBH, DBDH or BIPBH are effective in removing 100 mg/dL ascorbic acid within 10 seconds. The hydroperoxides are ineffective alone (without Cu(II)-histamine-Gantrez added as a catalyst).

TABLE V

| Tube No. | $H_2O$ | 0.5 M Phosphate (pH 7.0) | 0.2 M Cu(II)-Histamine Gantrez | 0.1 M Co-Oxidant | 2 K mg/dL Glucose | 10% Ascorbic Acid | Results Glucose Strip | C-STIX |
|---|---|---|---|---|---|---|---|---|
| 1 | 0.39 mL | 0.4 mL | 50 μL | 0.1 mL CBH | 50 μL | 10 μL | Blue | negative |
| 2 | 0.39 | " | " | 0.1 mL IBH | " | " | Blue | negative |
| 3 | 0.39 | " | " | 0.1 mL DBDH | " | " | Blue | negative |
| 4 | 0.39 | " | " | 0.1 mL BIPBH | " | " | Blue | negative |
| 5 | 0.49 | " | " | — | " | " | No Color | positive |
| 6 | 0.44 | " | — | 0.1 mL CBH | " | " | No Color | positive |
| 7 | 0.44 | " | — | 0.1 mL IBH | " | " | No Color | positive |
| 8 | 0.44 | " | — | 0.1 mL DBDH | " | " | No Color | positive |
| 9 | 0.44 | " | — | 0.1 mL BIPBH | " | " | No Color | positive |
| 10 | 0.54 | " | — | — | " | " | No Color | positive |
| 11 | 0.55 | " | — | — | " | — | Blue | negative |

Example 5

Liquid Assay to Screen Oxidants II

The oxidants II were screened in a liquid assay for their reactivities as ascorbic scavengers. The general procedures are as follows:
1. The oxidants were mixed with buffer solution in a 12×75 mm test tube.
2. Glucose and ascorbic acid solutions were added and the mixture was mixed for about 10 seconds.
3. Glucose strips (containing TMB, glucose oxidase and peroxidase impregnated from solution of 100 mM, 300 unit/mL and 500 unit/mL, respectively, in buffer, MES (4-morpholine ethane sulfonic acid), pH 6; paper: Whatman 54) was then dipped into the mixture and the color development rate was recorded.
4. Controls were run in which the oxidants or glucose or ascorbic acid were absent.

TABLE VI

Copper Polymer System-Cu(II)-Histamine-Gantrez
Buffer: Phosphate, 0.4 M, pH 7
Glucose: 100 mg/dL
Ascorbic Acid: 100 mg/dL
Oxidant I: Cu(II)-Histamine-Gantrez: 12.5 mM
Solubility of Oxidant I: Insoluble, homogeneous TABLE VI-continued

| Oxidant II | Concentration mM | Reactivity[b] |
|---|---|---|
| — | — | ++ |
| $O_2$[a] | bubble 20 sec. | ++++ |
| Air | bubble 20 sec. | ++ |
| $K_2CrO_4$ | 2.5 | ++++ |
| $Th(NO_3)_3$ | 3.5 | ++++ |
| $KBrO_3$ | 66 | ++++[c] |
| $Ce(SO_4)_2$ | 2.5 | +++ |
| $Hg(NO_3)_2$ | 4 | ++++[c] |
| $MnO_2$ | 10 | ++++ |
|  | 7.5 | +++ |
| 1-Chlorobenzotriazole | 1 | ++++ |
| DBDH | 5 | ++++ |

[a]A control reaction was run in which no Cu(II)-Histamine-Gantrez was present and the reactivity is negative indicating that $O_2$ alone does not have enough activity to remove ascorbic acid interference.
[b]Reactivity was measured within 10 seconds after mixing (see c, d, e).
[c]++++ means reactivity of the glucose test strip is equal to that observed when the strip is dipped into control containing no ascorbic acid.
[d]+++ means slightly less reactivity.
[e]++ means activity less than +++.
[f]Reactivity was measured after 5 minutes incubation at room temperature.

Example 7

Examples of various concentrations of oxidant I and oxidant II. Procedures followed were the same as those in Example 5.

Buffer: Phosphate, 0.4 M, pH 7
Glucose: 100 mg/dL
Ascorbic Acid: 100 mg/dL
Oxidant I: Cu(II)-Histamine-Gantrez

| Concentration of Oxidant I, mM | Oxidant II Compound | Concentration mM | Reactivity |
|---|---|---|---|
| 12.5 | DBDH | 5 | ++++ |
| 12.5 | DBDH | 10 | ++++ |
| 12.5 | DBDH | 20 | ++++ |
| 10 | $K_2CrO_4$ | 5 | ++++ |
| 12.5 | $K_2CrO_4$ | 1.5 | +++ |
| 12.5 | $K_2CrO_4$ | 2.5 | ++++ |
| 20 | $K_2CrO_4$ | 20 | ++++ |

The present invention is defined by the claims which are provided below, and the foregoing discussion is merely provided to help understand the claims and understand the numerous possible embodiments of the present invention as defined by the claims. The limitations defining this invention are expressly outlined in the claims, and nothing provided in the foregoing discussion is intended to provide any additional limitations thereto.

What is claimed is:

1. An ascorbate scavenger system, said system consisting essentially of:
   a first oxidant comprising a water soluble polymer containing a first part selected from the group consisting of polymethyivinylethermaleic acid, polyacrylic acid and polyaspartic acid and a second part selected from the group consisting of imidazole, pyridine and 2,2'-bipyridine, said polymer being complexed with $Cu^{+2}$ to obtain a copper/ligand complex; and
   a second oxidant consisting of an inorganic oxidant, organic peroxide or 1-halobenzotriazole.

2. The system of claim 1 wherein the second oxidant further comprises chromate, bromate, iodate, thallium (III), ceric (IV) mercuric compounds, manganese (III) compounds, diisopropylbenzene dihydroperoxide (DBDH), phenylcyclohexane hydroperoxide, p-(α-hydroperoxyisopropyl)benzoic acid, p-bromoisopropyl)benzene hydroperoxide, p-(α-hydroxy-α'-hydroperoxyisopropyl)benzene, or 1-halobenzotriazole.

3. A method for scavenging ascorbate in a redox reagent system, said method comprising the steps of:
   combining a first oxidant consisting essentially of a water soluble polymer containing a first part selected from the group consisting of polymethylvinylether-maleic acid, polyacrylic acid and polyaspartic acid and a second part selected from the group consisting of imidazole, pyridine and 2,2'-bipyridine, said polymer being complexed with $Cu^{+2}$ to obtain a copper/ligand complex with a second oxidant consisting of an inorganic oxidant, organic peroxide or 1-halobenzotriazole and combining the resulting mixture with the redox reagent system.

4. The method of claim 3 wherein the second oxidant further comprises chromate, bromate, iodate, thallium (III), ceric (IV) mercuric compounds, manganese (III) compounds, diisopropylbenzene dihydroperoxide (DBDH), phenylcyclohexane hydroperoxide, p-(α-hydroperoxyisopropyl)benzoic acid, p-bromoisopropyl)benzene hydroperoxide, p-(α-hydroxy-α'-hydroperoxyisopropyl)benzene, or 1-halobenzotriazole.

* * * * *